United States Patent [19]

Thorne et al.

[11] Patent Number: 5,573,760

[45] Date of Patent: Nov. 12, 1996

[54] METHODS AND COMPOSITIONS TO MONITOR AND CONTROL TERMITES

[76] Inventors: Barbara L. Thorne, 4306 Woodbury St., University Park, Md. 20782-1173; James F. A. Traniello, 11 Smith Ave., Lexington, Mass. 02173

[21] Appl. No.: 163,228

[22] Filed: Dec. 7, 1993

Related U.S. Application Data

[63] Continuation-in-part of Ser. No. 941,472, Sep. 8, 1992, abandoned.

[51] Int. Cl.$^6$ .................................................. A01N 25/00
[52] U.S. Cl. ................................................................ 424/84
[58] Field of Search .............................. 424/84, 488, 479, 424/470, 409, 410, 408, 195.1

[56] References Cited

U.S. PATENT DOCUMENTS

| | | | |
|---|---|---|---|
| 3,070,495 | 12/1962 | Esenther et al. | 424/2 |
| 3,220,921 | 11/1965 | Greenbaum et al. | 514/755 |
| 3,624,953 | 12/1971 | Crosby | 43/131 |
| 3,794,034 | 2/1974 | Jones, Sr. | 604/360 |
| 3,858,346 | 1/1975 | Bailey | 43/124 |
| 4,065,347 | 12/1977 | Aberg et al. | 162/26 |
| 4,201,551 | 5/1980 | Lyshkow et al. | 44/10 |
| 4,363,798 | 12/1982 | D'Orazio | 424/84 |
| 4,599,138 | 7/1986 | Lindahl | 162/19 |
| 4,642,287 | 2/1987 | Inoi et al. | 435/99 |
| 4,842,877 | 6/1989 | Tyson | 426/271 |
| 5,009,789 | 4/1991 | Helmer et al. | 210/641 |
| 5,073,612 | 12/1991 | Irie et al. | 526/240 |
| 5,246,936 | 9/1993 | Treacy et al. | 514/256 |

FOREIGN PATENT DOCUMENTS

| | | |
|---|---|---|
| 1319401 | 12/1989 | Japan . |
| 8407773 | 4/1985 | South Africa . |
| 1597293 | 9/1981 | United Kingdom . |

OTHER PUBLICATIONS

Stapleton, "Renal uric acid clearance in human neonates," The Journal of Pediatrics, 103(2):290–294 (Aug. 1983).
Beal et al., Resistance of Wood From Paraquat–Treated Southern Pines to Subterranean Termites, . . . , Forest Products J. 29(4):35–38 (Apr. 1979).
Beal, Preventing Termite Attack by Adding Insecticide to Particleboard, . . . , Forest Products J. 29(12):29–34 (Dec. 1979).
Esenther et al., Insecticidal Baits on Field Plot Perimeters Suppress *Reticulitermes*, J. Econ. Entomol. 71(4):604–607 (Aug. 1978).
Webster's New Collegiate Dictionary (1977), USA, pp. 112 and 1203.
La Fage et al., "Nutrient dynamics of termites," Production Ecology of Ants and Termites, pp. 165–233 (Dec. 1977).
Logan et al., "Laboratory trials on the toxicity of hydramethylnon (Amdro; AC 217,300) to *Reticulitermes santonensis* Feytaud Isoptera: Rhinotermitidae and *Microtermes lepidus* Sjostadt Isopterma Termitidae" Bulletin Entomol. Research 80(1):19–26 (Mar. 1990) (Biosis Abstract).

Esenther et al., Termite Control: Decayed Wood Bait, Sociobiology 4(2):215–222 (Jun. 1979).
Esenther et al., Attractant–Mirex Bait Suppresses Activity of *Reticulitermes* Spp., J. Econ. Entomol. 67(1):85–88 (Feb. 1974).
Spears et al., "Survival and Food Consumption by the Desert Termite *Gnathamitermes tubiformans* in Relation to Dietary Nitrogen Source and Levels" Environ. Entomol. 5(5):1022–1025 (Oct. 1976) (Biosis Abstract).
Potrikus et al., "Uric Acid in Wood Eating Termites," Insect Biochem., 10(1):19–28 (Mar. 1980). (Biosis Abstract).
M. Tamashiro, et al., A Simple Method to Observe, Trap, and Prepare Large Numbers of Subterranean Termites for Laboratory and Field Experiments, Environmental Entomology, vol. 2, No. 4, pp. 721–722, (1973).
Dr. L. G. E. Kalshoven, The Ability of Coptotermes to Locate Exposed Timber, Idea, vol. 10, Part 3, 16, II, pp. 43–49, (1955).
N. Su and R. H. Scheffrahn, A Method to Access, Trap, and Monitor Field Poplars of the Formosan Subterranean Termite in the Urban Environment, Sociobiology. vol. 12 (No. 2), pp. 298–304, (1986).
F. L. Carter and T. R. Dell, Screening Selected American Hardwoods for Natural Resistance to a Native Subterranean Termite, USDA Southern Forest Experiment Station Research Paper, pp. 1–10, (1981).
R. F. Smyth, F. L. Carter, Cyril C. Baxter, Influence of Wood Decay on Feeding and Survival of the Eastern Subterranean Termite, Crawford: Comparative Reproduction, pp. 59–62, (1971).
Mauldin et al. "Rearing two Subterranean Termites, *Reticulitermes flavipes* and *Captotermes formosanus*, on Artificial Diets", *Entomological Society of America* 68(1), pp. 454–456 (1975).
Yusef et al. "Particleboard from acetylated albizzia particles", Mosukai Gakkaishi (1989), 35(7), 633–9.
Daniel Ben–Ghedalia et al. "Effect of Ozone and Ammonium Hydroxide Treatments on the Composition an *In vitro* Digestibility of Cotton Straw" J. Sci. Food Agric. 31 1337–1342 (Dec. 1980).
Webster's New Collegiate Dictionary G&C Merrian Co. p. 421 (1977, month unavailable).

*Primary Examiner*—Jeffrey C. Mullis
*Attorney, Agent, or Firm*—John W. Hogan, Jr.

[57] ABSTRACT

The present invention provides compositions for monitoring termites which comprise a substantially nontoxic, highly palatable cellulose source, which is effective for an early diagnosis of termite activity or termite infestation, an exogenous nitrogen source utilizable by termites and optionally, water and a suitable binding medium. The present invention further provides compositions for controlling termites which contain pesticidal agents in combination with the aforesaid monitoring composition. Additionally, the present invention provides methods of monitoring the presence of termites and controlling termites if infestation has occurred.

11 Claims, 1 Drawing Sheet

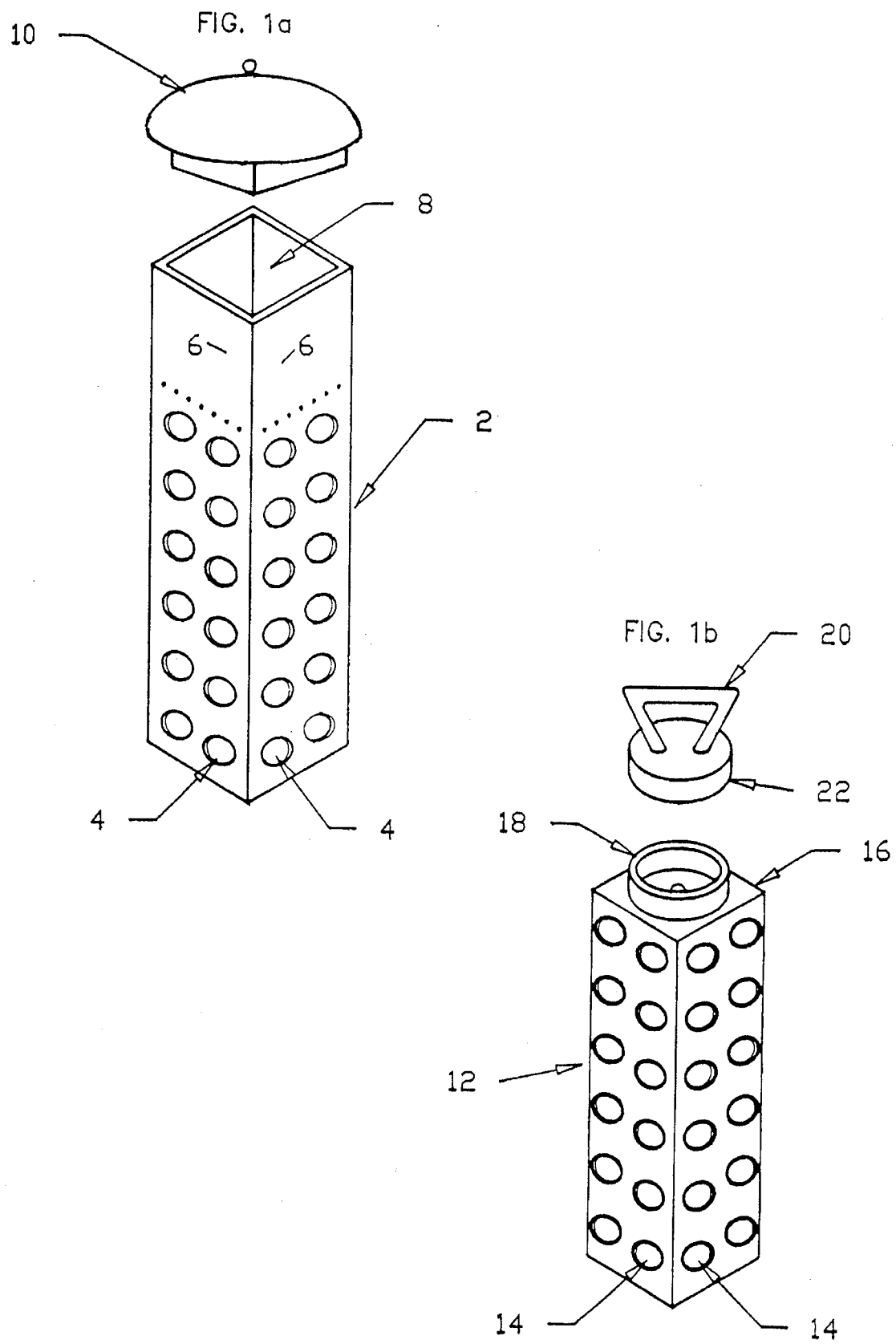

1

METHODS AND COMPOSITIONS TO MONITOR AND CONTROL TERMITES

BACKGROUND OF THE INVENTION

This application is a continuation-in-part of the copending U.S. application, Ser. No. 07/941,472, filed on Sep. 8, 1992, now abandoned.

DESCRIPTION OF THE RELATED ART

Termites, known for their destructive activity, are responsible for approximately 1 billion dollars damage to building each year. The onset of the termite activity is generally difficult to detect and control since the destruction occurs internally within wooden structures and may provide no external signs of damage until termite infestation has caused significant destruction.

Generally, prevention of termite destruction has focussed on how to deter termites such as, for example, coating or treating the wood used in building the structure with materials which termites dislike; digging a trench around the perimeter of a home and depositing a pesticide within the trench; or pressure injecting a pesticide to protect a home. However, these methods advocate the indiscriminate use of toxicants without the benefit of preliminary monitoring of the area to determine if and where termites are present.

SUMMARY OF THE INVENTION

The present invention relates to methods and compositions for monitoring termite infestations and a method for controlling termites if an infestation has occurred. More specifically, the present monitoring composition includes a nontoxic, highly palatable cellulose source, a nitrogen source, water and, optionally, a suitable binding medium. The monitoring method provides placing the monitoring composition in a device such as a cartridge having at least one hole, allowing entry by termites into the cartridge, near the locus of the suspected termite activity and later checking the cartridge for termites or signs of termites. If termites have infested the cartridge, controlling the termites is accomplished by replacing the first cartridge with a second cartridge which, in addition to the monitoring composition, includes a pesticide.

BRIEF DESCRIPTION OF THE DRAWINGS

The background of the invention and its departure from the art will be further described hereinbelow with reference to the accompanying drawings, wherein:

FIG. 1a shows a perspective view of one embodiment of a fixed outer housing of a subterranean termite monitoring and control station; and FIG. 1b shows a perspective view of one embodiment of a removable cartridge receivable within the housing illustrated by FIG. 1a.

DETAILED DESCRIPTION OF THE PREFERRED EMBODIMENTS

The monitoring composition, and method, unlike the past methods of monitoring or deterring termites, utilize natural foraging and other social behaviors of the termite as a way of locating termite activity and targeting the termite colony with an insecticide. The composition is designed so that if termites encounter it, they will recruit nestmates, occupy the composition and consume it in preference to the structure to be protected. Rather than focusing on what termites dislike, the present invention is concerned with what termites need and prefer to eat, and therefore want instinctively to occupy and consume.

Termites are primarily known for eating wood. However, wood generally contains both cellulose which termites use and lignin which is largely or totally indigestible to many species of termites. Therefore, the monitoring composition preferably contains wood with a high cellulose to lignin ratio such as, for example, about 3:1 to about 5:1, or higher.

While decayed wood is appealing to termites, different types of wood are subject to different kinds of decay. Fungi play a prominent role in wood degradation, but there are many types of fungi which may exist in numerous combinations of species on decaying wood, and therefore produce a very large number of possible by-products during decay. The products of fungal decay and their ability to affect the palatability and consumption of wood by termites and termite survivorship are dependent on the species of tree and its own unique wood chemistry as well as the species of fungi that contribute to its decay and the metabolites that the fungi produce.

Additionally, several secondary plant compounds present in different species of trees deter termite feeding or decrease termite survivorship. For example, black cherry wood, while having a high cellulose to lignin ratio of about 4:1, contains an undesirable 4.5% tannin content and produces a toxic, defensive chemistry consisting of cyanogen glycosides. Similarly, aspen wood produces toxic secondary compounds such as phenol glycoside and tricocarpin on degradation by fungi. By adversely affecting termite feeding or survivorship, the presence of the secondary compounds is an obstacle for monitoring termites. Thus, the monitoring composition preferably contains wood that has few, if any, undesirable, naturally occurring chemicals.

In accordance with the present invention, the composition for monitoring termites provides a substantially nontoxic, highly palatable cellulose source. The term "substantially nontoxic" means that the cellulose source will preferably not kill the termites but may contain traces of slow-acting, toxic secondary compounds or other defensive chemistry. The term "highly palatable" refers to the appropriate cellulose source which is preferred by the termites, stimulates their feeding and does not contain any natural substance that will deter the termites from consuming the food source. By this term, it is intended that the food source will be pleasing and nutritious to the termites such that the termites will occupy and recruit to the food source. Beneficially, the cellulose source of the present invention is highly effective for an early or rapid diagnosis of termite activity or termite infestation. Consequently, one will be able to efficiently and rapidly determine the presence of the termites to establish a prophylactic diagnosis or to obtain effective treatment after infestation. By minimizing structural damage to buildings or homes through early or rapid diagnosis of the termite problem, the cellulose source of this invention provides an important advantage over the use of standard termite-monitoring agents, such as pine in pine stakes or pine-based traps, which require months to be located by termites and are not immediately consumed in large quantities.

Out of the thousands of tree species, it is surprisingly found that birch (Betula) has the valuable characteristics sought by the present invention. It has a high cellulose to lignin ratio of about 4.3:1, no tannin content and no defensive chemistry which provides secondary compounds that deter termite feeding or affect termite survivorship. Birch is a highly palatable, nutritious and attractive food source that stimulates recruitment and consumption. Decay of birch by certain types of fungi dramatically increases its palatability to termites and further enhances its nutritional value. White birch (*Betula papyrifera*) is especially preferred.

The cellulose source of the present invention may be totally or partially synthetic in origin. The cellulose source of the present invention may further include mixtures of different suitable wood species, processed or purified cellulose and/or derivatives of cellulose such as methoxylated cellulose. For example, it may be advantageous for marketable products to employ commercially available forms of processed or purified cellulose such as microcrystalline or microgranular cellulose either alone or mixed with small amounts of birch, decayed birch or partially decayed birch, with decayed birch being particularly preferred.

In addition to cellulose, termites usually need moisture and nitrogen and, therefore, the monitoring composition preferably includes water and an exogenous nitrogen source utilizable by termites, such as urea, uric acid, amino acids, peptides, proteins and the like. The addition of a nitrogen source, in accordance with the present invention, significantly increases recruitment, initiation of consumption and rate of utilization of the monitoring composition. Finally, the monitoring composition can optionally incorporate a suitable binding medium including nutrient mediums such as agar, an agar/water gel mixture, etc., or simply binding agents such as lignin sulfonate and the like.

It should be appreciated that the monitoring composition can be prepared or used as a dry blend. For example, rotted wood can be dried and formulated as a dry product to lessen the degree of mold growth. If desired, the consumer then adds water to the dry blend prior to application or during use with the assistance of a suitable wick. Typically, about 75% of water is mixed with about 25% of the dry blend. Alternatively, the dry blend may be utilized directly in the target area without the addition of any water. Under those conditions, the environment supplies moisture through rain and the like. While termites prefer the moisture, they will still consume the dry product but to a lesser extent.

The proportions of the above mentioned components of the monitoring composition are flexible. The percentage of the exogenous nitrogen source is important because termites can be repelled by too much nitrogen. Generally, a preferred composition includes, on a weight basis, about 0.25% to about 5% of uric acid, about 20% to about 95% birch (preferably about 20% to about 45%), 0% to about 1% agar (preferably about 0.1% to about 1%) and 0% to about 75% water (preferably about 50% to about 75%). Another preferred embodiment comprises, on a weight basis, about 0.5% to about 5% of uric acid, about 15% to about 40% purified cellulose, about 1% to about 5% of decayed or partially decayed birch and about 50% to about 75% water.

It is important to note that the monitoring composition does not attract termites per se. One would not want to attract termites and create a problem where none existed before. However, because termites prefer consuming the monitoring composition, once the termites discover it, they will return to it and recruit others from the colony. Subterranean termites tunnel underground and will tunnel into the monitoring composition. The termites will stimulate other colony members to use the food, then return to the colony and share the food. These behavioral patterns are utilized to great advantage in the monitoring and controlling methods of the present invention.

The monitoring method of the present invention includes placing the monitoring composition within a perforated cartridge removably received within a perforated outer housing, said cartridge having at least one hole or a plurality of holes to allow access to the cartridge near the locus of the suspected termite activity. The outer housing is permanently situated in the location to be monitored and the cartridge containing the monitoring composition is placed within the outer housing. The cartridge is subsequently checked for termites, signs of termites or termite damage.

One example of an apparatus for monitoring and detecting termite infestation useful in the present invention is disclosed and claimed in U.S. patent application Ser. No. 07/941,460, filed on Sep. 8, 1992. For purposes of illustration, the apparatus may have a housing adapted to being permanently positioned relative to a predetermined target area where it is desirable to monitor termite activity such as at or below ground level around the perimeter of a building or home. The housing is perforated with at least one hole or a plurality of holes. FIG. 1a shows a perspective view of a housing useful in the present method of monitoring and controlling termites. A substantially hollow rectangular shaped housing generally illustrated by reference numeral 2 defines a plurality of apertures 4 on portions of each outer side surface of the housing. The housing is typically composed of a durable, corrosion resistant material, for example, an acrylic or high strength plastic. The upper portions 6 of each side of the housing are imperforate and the top surface 8 of the housing is opened. A cap 10 is removably received on the top surface 8 to close the housing 2.

A first cartridge, which is perforated by at least one hole or a plurality of holes, is removably received within the housing. The cartridge and the housing may be formed in the same geometrical configuration such as a rectangular shape. FIG. 1b shows a typical cartridge useful in the practice of the present invention, designated generally by the reference numeral 12, which is configured as a solid rectangle to complement the configuration of the housing 2. The illustrated cartridge defines a plurality of openings 14 on each of its outer surfaces which are aligned with the corresponding openings 4 on the housing 2 when the cartridge 12 is received in an operational position within the housing 2. The outer width of the cartridge 12 is slightly less than the inner width of the housing 2 so that the cartridge may be removably received in a close fitting relationship within the housing. A circular threaded flange 18 extends upwardly from the top surface 16 of the cartridge, and a handle 20 having a complementary threaded base portion 22 is removably securable to the flange be by complementary screw threads. Preferably, the length of the cartridge 12 when the handle 20 is mounted to the top thereof is less than the length of the housing 2 so that the cartridge and the handle can be received within the housing in a manner which will not interfere with placement of the cap be to cover the top surface of the housing 2. The cartridge, which will contain the monitoring composition of the present invention, further provides a centrally disposed wick extending longitudinally through the cartridge for retaining or adding moisture to the cartridge from a refillable water reservoir. Usually, the cartridge is transparent for direct inspection of termite consumption and occupancy.

When the cartridge is fully received within the housing in a predetermined operational position, the respective opening(s) in the cartridge and the housing are oriented in such a fashion as to be at least in partial alignment with each other. The first cartridge includes the monitoring composition of the present invention which is utilized to induce termite feeding and to indicate the presence of the subterranean termites which forage and burrow into the cartridge through the aligned hole(s) in the cartridge and housing. Each cartridge has an internal moisture source such as a wick which provides continuous slow-release moisture to the monitoring composition, preferably through a refillable water supply. The first cartridge is at least in part transparent such that it may be periodically removed from the housing and inspected for termite activity or presence. If there is no termite activity detected, the first cartridge may be returned to the housing for future monitoring. If termite activity or presence is detected, the first cartridge may be replaced by a second interchangeable cartridge which is designed similar to the first cartridge in that it is removably received within the outer housing and has at least one opening or a plurality of holes which can be oriented in at least a partial alignment with the opening(s) in the housing when the second cartridge is received in a predetermined operational position within the outer housing. The first or second cartridge may contain a pesticide in admixture with the monitoring composition of the invention.

The substitution of the second cartridge will not disturb the passageways or tunnels established by the termites to the outer housing from the termite colony because the housing remains permanently positioned in the terrain. When the cartridge is placed within the housing, the alignment of the hole(s) affords the termites with continued access to the monitoring or pesticidal composition.

After allowing the termites, if any, an opportunity to locate the monitoring composition, the cartridge is removed and checked for visual signs of termites. Such signs include observing termites consuming the composition, tunnels left by termites or any other signs known to indicate the presence of termites. Proper placement of the cartridge or cartridges is naturally important. A single cartridge may not be discovered by termites and thus a plurality of cartridges are generally used in accordance with the present invention. Advantageously once the monitoring cartridges have been placed, they may be checked and rechecked until termite activity has been found. Indiscriminate use of pesticides is avoided because no pesticide or toxicant is used until termites have been located.

If termite presence is detected in the method of monitoring termites, the cartridge may be replaced with a second cartridge, as described above, which includes a composition for the control of termites containing a pesticidally effective amount of a pesticide mixed with the monitoring composition. Suitable pesticides include, but are not limited to, slow-acting toxicants, insect growth regulators, pathogens and the like. The second cartridge preferably has an identical hole placement as the first cartridge. By replacing the second cartridge exactly where the first has been and by having the identical or nearly identical hole placement, the tunnels in the soil or wooden beam leading to the cartridge are not disturbed. A slow-acting toxicant or pesticide is preferable because the termites gathering the food then bring the insecticide back to the colony and transfer it to colony members that have not fed directly at the cartridge, thus reducing the size of the colony. A particularly useful pesticide in the practice of this invention is a termiticide such as hydramethylnon.

In addition to monitoring subterranean termites, the aforementioned apparatus may also be used to monitor termites on the external surface of various wood structures. Under those circumstances, the perforated outer housing may be mounted onto the surface of a wooden structure to be monitored and/or treated such as, for instance, directly on a wooden beam of a house. Here, only the surface of the housing in contact with the surface of the wooden structure is perforated since termites can only enter the housing through the housing surface adjacent to the wood surface to which the housing is mounted. The housing is specially adapted to receive the cartridges containing the monitoring composition with or without a pesticidal agent wherein the cartridges have opening(s) which are oriented in alignment with the openings in the housing when the cartridges are fully inserted into the housing. The housing is mounted onto the surface of the wooden structure and the cartridges can be removed and inserted periodically within the housing to inspect for termite activity and to treat termite infestation as needed.

In order to facilitate a further understanding of the invention, the following examples are presented primarily for the purpose of illustrating certain specific details thereof. The invention is not to be deemed limited thereby except as defined in the claims.

EXAMPLE 1

Preparation of Monitoring Composition

In 750 mL boiling water, 9.5 g of agar is dissolved. The mixture is cooled to the point that it begins to gel.

The bark is removed from decayed white birch (*Betula papyrifera*). The wood is placed in a high powered blender with water in approximately a volume ratio of 1 part water to 3 parts wood. The wood and water are blended thoroughly until a uniform paste material is achieved. The wet paste is towel dried to remove excess liquid. The birch paste is combined with the agar mixture in a 4:1 volumetric ratio (birch paste to agar mixture). After combining the birch paste and agar mixture, uric acid is added in a wet weight ratio of one part uric acid to 99 parts birch paste/agar mixture.

EXAMPLE 2

Preparation of Termiticide Composition

The diagnostic monitoring composition of Example 1 is prepared and 0.25% hydramethylnon, a delayed-action toxicant, is added to form the termiticide composition.

EXAMPLE 3

Field Comparison of Pine to Birch

Nineteen locations are selected to monitor for termite infestation. In each location pine stakes and decayed birch monitoring compositions are placed in the ground to compare the response of termites to pine (the building material generally used in wooden houses) to birch (the wood used in the diagnostic monitoring composition of Example 1). Ten to seventy days later the stakes are checked for the degree to which they are utilized by termites. This is done by estimating the number of termites at the monitoring composition to the nearest order of magnitude.

The results are displayed in Table 1.

TABLE 1

| Location | Pine | Birch |
| --- | --- | --- |
| 1 | 0 | >1,000 |
| 2 | 0 | >1,000 |
| 3 | 0 | >1,000 |
| 4 | 0 | >1,000 |
| 5 | 0 | >1,000 |

TABLE 1-continued

| Location | Pine | Birch |
|---|---|---|
| 6 | ≦10 | >1,000 |
| 7 | 0 | >1,000 |
| 8 | ≦10 | >1,000 |
| 9 | ≦10 | >1,000 |
| 10 | 0 | >1,000 |
| 11 | 0 | >1,000 |
| 12 | 0 | >100 |
| 13 | ≦10 | >100 |
| 14 | 0 | >100 |
| 15 | 0 | >100 |
| 16 | 0 | >1,000 |
| 17 | 0 | >100 |
| 18 | 0 | >100 |
| 19 | 0 | >100 |

EXAMPLE 4

Nitrogen Supplementation

Two monitoring compositions are prepared in accordance with example 1 except that the second does not have any uric acid added. The compositions are placed in a Petri dish with termites and observed to count the number of termites on each composition at different times. The results are listed in Table 2.

TABLE 2

| Observation time: | | # Termites on composition $N_2$ | |
|---|---|---|---|
| Day: | (hr) | + | − |
| 1 | 01:00 | 15 | 6 |
|   | 02:00 | 4 | 7 |
|   | 09:00 | 10 | 0 |
|   | 19:00 | 10 | 1 |
|   | 21:00 | 8 | 1 |
|   | 22:00 | 7 | 1 |
|   | 22:30 | 5 | 2 |
|   | 23:00 | 6 | 0 |
|   | 24:00 | 8 | 0 |
| 2 | 00:30 | 9 | 1 |
|   | 01:00 | 8 | 0 |
|   | 10:30 | 9 | 7 |
|   | 11:00 | 8 | 12 |
|   | 12:00 | 9 | 3 |
|   | 13:30 | 15 | 8 |
|   | 14:30 | 6 | 5 |
|   | 15:30 | 5 | 4 |
|   | 17:00 | 13 | 5 |
|   | 18:00 | 10 | 4 |
|   | 19:30 | 10 | 6 |
|   | 20:00 | 8 | 4 |
|   | 21:00 | 20 | 3 |
|   | 22:00 | 12 | 3 |
|   | 23:00 | 10 | 2 |
|   | 24:00 | 15 | 9 |
| 3 | 18:30 | 13 | 7 |
|   | 19:00 | 10 | 8 |
|   | 21:00 | 15 | 7 |
|   | 22:00 | 13 | 8 |
|   | 24:00 | 16 | 12 |
| 4 | 21:00 | 19 | 9 |
|   | 22:00 | 27 | 9 |
| 5 | 21:00 | 12 | 4 |
|   | 24:00 | 14 | 3 |
| 6 | 12:30 | 11 | 8 |
|   | 14:30 | 6 | 5 |
|   | 17:30 | 6 | 4 |
|   | 22:00 | 10 | 6 |
| 7 | 10:00 | 8 | 3 |
|   | 20:00 | 18 | 5 |
|   | 22:30 | 15 | 2 |
|   | 23:30 | 10 | 6 |
| 8 | 10:00 | 12 | 9 |
|   | 22:00 | 10 | 4 |
| 9 | 10:00 | 12 | 5 |
|   | 12:30 | 7 | 4 |
|   | 20:00 | 13 | 5 |
|   | 24:00 | 10 | 4 |
| 10 | 10:30 | 12 | 6 |
|   | 20:00 | 13 | 5 |

EXAMPLE 5

Secondary Kill

A group of 100 termites is allowed to feed at a toxic monitoring composition for 24 or 48 hours. The concentration of hydramethylnon is 0.5% and 2% in the replicates carried out. At the end of the 24 hour or 48 hour exposure period, 30 termites are removed from each group and placed in a new nest with 70 termites that have had no exposure to toxicant-containing food. Mortality is then recorded in these colonies. If cumulative mortality exceeds 30, it is evidence that the toxicant has been transferred from the exposed termites to the non-exposed termites by social food flow. That is, termites that have fed on toxic food regurgitate a portion of that food to other colony members. Therefore, termites are killed indirectly; all members of a colony do not need to feed directly at a toxicant-containing monitoring composition for control of the entire colony to be effective.

The results are listed in Table 3.

TABLE 3

SECONDARY KILL
Cumulative % Mortality

| TREATMENTS | DAYS AFTER EXPOSURE | | | | | | | | | |
|---|---|---|---|---|---|---|---|---|---|---|
| | 1 | 2 | 3 | 4 | 5 | 6 | 7 | 8 | 9 | 10 |
| A24 CONTROL | 0 | 2 | 2 | 3 | 3 | 3 | 3 | 3 | 3 | 5 |
| B24 2% | 0 | 2 | 3 | 3 | 7 | 12 | 25 | 47 | 70 | 77 |
| C24 2% | 2 | 2 | 8 | 8 | 8 | 8 | 10 | 17 | 42 | 65 |
| D24 .5% | 0 | 5 | 5 | 5 | 8 | 8 | 10 | 12 | 12 | 15 |
| E24 .5% | 0 | 2 | 5 | 5 | 5 | 7 | 7 | 7 | 10 | 12 |
| A48 CONTROL | 0 | 2 | 2 | 2 | 2 | 2 | 2 | 3 | 3 | 7 |
| B48 2% | 15 | 20 | 25 | 35 | 45 | 52 | 57 | 57 | 58 | 60 |
| C48 2% | 2 | 7 | 15 | 15 | 15 | 22 | 27 | 37 | 50 | 58 |
| D48 .5% | 0 | 10 | 22 | 23 | 23 | 23 | 23 | 25 | 28 | 33 |
| E48 .5% | 0 | 2 | 13 | 13 | 17 | 17 | 18 | 20 | 33 | 50 |

EXAMPLE 6

Control of Termites

Two monitoring compositions are made in accordance with Example 1 except that to the first is added 0.1% hydramethylnon and to the second is added 0.25% hydramethylnon. A third monitoring composition with no hydramethylnon acts as the control composition. These are separately employed to treat termite colonies consisting of 75, 100, and 100 termites respectively.

The results are listed in Table 4.

0.5% or 2% hydramethylnon, and the time course of mortality is followed. The results (Table 5) show that termites conditioned to feed on diagnostic monitoring composition do not discriminate against the same monitoring composition when hydramethylnon is added.

The results are listed in Table 5.

TABLE 4

| | Treatment 0.1% | | Treatment 0.25% | | Control |
|---|---|---|---|---|---|
| DAYS | MORTALITY | CUM. % | MORTALITY | CUM. % | MORTALITY |
| 1 | 0 | 0 | 0 | 0 | 0 |
| 2 | 0 | 0 | 0 | 0 | 0 |
| 3 | 0 | 0 | 0 | 0 | 0 |
| 4 | 0 | 0 | 0 | 0 | 0 |
| 5 | 3 | 4% | 3 | 3% | 0 |
| 6 | 0 | 4% | 0 | 3% | 0 |
| 7 | 0 | 4% | 2 | 5% | 0 |
| 8 | 0 | 4% | 2 | 7% | 0 |
| 9 | 0 | 4% | 0 | 7% | 0 |
| 10 | 0 | 4% | 0 | 7% | 0 |
| 11 | 1 | 5.3% | 0 | 7% | 0 |
| 12 | 0 | 5.3% | 12 | 19% | 0 |
| 13 | 0 | 5.3% | 12 | 31% | 0 |
| 14 | 7 | 14.6% | 0 | 31% | 0 |
| 15 | 4 | 20.0% | 67 | 98% | 0 |
| 16 | 5 | 26.7% | 2 | 100% | 0 |
| 17 | 15 | 46.7% | — | — | 0 |
| 18 | 7 | 56.0% | — | — | 0 |
| 19 | 10 | 69.3% | — | — | 0 |
| 20 | 7 | 78.7% | — | — | 0 |
| 21 | 5 | 85.3% | — | — | 0 |
| 22 | 4 | 90.6% | — | — | 0 |
| 23 | 7* | 100.0% | — | — | 0 |

*Because some termites die during the course of the experiment and are consumed by nestmates, all termites are counted at the end of the test. The number that have been consumed by nestmates is added to the final mortality count. One hundred percent of the termites are dead on day 23.

EXAMPLE 7

Control of Termites

Termites from two locales are allowed to feed on the monitoring composition for a period of seven days. They are then offered a monitoring composition containing either

TABLE 5

| TREATMENTS | DAYS AFTER EXPOSURE | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | |
| REPLICATE 1 | | | | | | | | | | | | | |
| A CONTROL | 3 | 4 | 4 | 4 | 4 | 4 | 4 | 4 | 4 | 4 | 5 | 5 | |
| B 2% HM | 25 | 79 | 94 | 94 | 96 | 97 | 98 | 100 | — | — | — | — | |
| C 2% HM | 27 | 67 | 84 | 84 | 87 | 89 | 91 | 92 | 93 | 95 | 100 | — | |
| D .5% HM | 4 | 6 | 26 | 26 | 26 | 31 | 35 | 41 | 47 | 51 | 62 | 100 | |
| E .5% HM | 0 | 0 | 4 | 4 | 9 | 14 | 15 | 19 | 24 | 29 | 39 | 100 | |
| | 1 | 2 | 3 | 4 | 5 | 6 | 7 | 8 | 9 | 10 | 11 | 12 | 13 |
| REPLICATE 2 | | | | | | | | | | | | | |
| A CONTROL | 2 | 2 | 2 | 2 | 2 | 2 | 2 | 2 | 2 | 2 | 2 | 2 | 2 |
| B 2% HM | 8 | 20 | 51 | 51 | 51 | 54 | 59 | 63 | 65 | 66 | 100 | — | — |
| C 2% HM | 15 | 45 | 67 | 67 | 68 | 70 | 72 | 72 | 73 | 80 | 84 | 100 | — |
| D .5% HM | 3 | 12 | 24 | 24 | 25 | 27 | 27 | 32 | 36 | 40 | 50 | 50 | 99 |
| E .5% HM | 1 | 1 | 5 | 7 | 8 | 15 | 16 | 20 | 24 | 30 | 37 | 97 | 100 |

In the foregoing, there has been provided a detailed description of particular embodiments of the present invention for the purpose of illustration and not limitation. It is to be understood that all other modifications, ramifications and equivalents obvious to those having skill in the art based on this disclosure are intended to be included within the scope of the invention as claimed.

What is claimed is:

1. A composition for controlling termites comprising a pesticidally effective amount of a pesticide and a monitoring composition; wherein the monitoring composition comprises, on a weight basis, about 20% to about 95% of a substantially nontoxic, highly palatable cellulose source for monitoring termites selected from the group consisting of decayed birch, partially decayed birch, processed cellulose, purified cellulose and a combination thereof, said cellulose source being effective for an early diagnosis of termite activity or termite infestation, about 0.25% to about 5% of an exogenous nitrogen source utilizable by termites selected from the group consisting of urea and uric acid, 0% to about 75% water and 0% to about 1% of a binding medium.

2. The composition according to claim 1 wherein the cellulose source comprises processed or purified cellulose in combination with decayed birch or partially decayed birch.

3. The composition according to claim 2 wherein the pesticide is a termiticide, an insect growth regulator or a pathogen.

4. The composition according to claim 3 wherein the termiticide is hydramethylnon.

5. A composition for monitoring termites comprising, on a weight basis, about 20% to about 95% of a substantially nontoxic, highly palatable cellulose source for monitoring termites selected from the group consisting of decayed birch, partially decayed birch, processed cellulose, purified cellulose and a combination thereof, said cellulose source being effective for an early diagnosis of termite activity or termite infestation, about 0.25% to about 5% of an exogenous nitrogen source utilizable by termites selected from the group consisting of urea and uric acid, 0% to about 75% water and 0% to about 1% of a binding medium, wherein the cellulose source comprises purified cellulose and the purified cellulose is microgranular or microcrystalline cellulose.

6. A composition for monitoring termites comprising, on a weight basis, about 20% to about 95% of a substantially nontoxic, highly palatable cellulose source for monitoring termites selected from the group consisting of decayed birch, partially decayed birch, processed cellulose, purified cellulose and a combination thereof, said cellulose source being effective for an early diagnosis of termite activity or termite infestation, about 0.25% to about 5% of an exogenous nitrogen source utilizable by termites selected from the group consisting of urea and uric acid, 0% to about 75% water and 0% to about 1% of a binding medium, wherein the cellulose source comprises decayed birch or partially decayed birch in combination with processed cellulose or purified cellulose.

7. The monitoring composition according to claim 6 wherein the birch is white birch.

8. The monitoring composition according to claim 7 comprising, on a weight basis, about 15% to about 40% of purified cellulose, about 1% to about 5% of decayed white birch or partially decayed white birch, about 0.5% to about 5% of the nitrogen source and about 50% to about 75% water.

9. A composition for monitoring termites consisting of, on a weight basis, about 20% to about 95% of a substantially nontoxic, highly palatable cellulose source for monitoring termites selected from the group consisting of decayed birch, partially decayed birch, processed cellulose, purified cellulose and a combination thereof, said cellulose source being effective for an early diagnosis of termite activity or termite infestation, about 0.25% to about 5% of an exogenous nitrogen source utilizable by termites selected from the group consisting of urea and uric acid, 0% to about 75% water and 0% to about 1% of a binding medium.

10. The monitoring composition according to claim 1 wherein the cellulose source is purified cellulose and the binding medium is agar, an agar/water gel mixture or lignin sulfonate.

11. The monitoring composition according to claim 1 consisting of, on a weight basis, about 20% to about 45% of purified cellulose, about 0.5% to about 5% of the nitrogen source and about 50% to about 75% water.

* * * * *

UNITED STATES PATENT AND TRADEMARK OFFICE
CERTIFICATE OF CORRECTION

PATENT NO.   : 5,573,760
DATED        : November 12, 1996
INVENTOR(S)  : Barbara L. Thorne; James F. A. Traniello It is certified that error appears in the above-indentified patent and that said Letters Patent is hereby corrected as shown below:

Column 12, line 55, claim 10, and line 59, claim 11, according to claim "1", each occurrence, should read according to claim --9--.

Signed and Sealed this

Fifteenth Day of December, 1998

Attest:

BRUCE LEHMAN

*Attesting Officer*       *Commissioner of Patents and Trademarks*